(12) United States Patent
Omenetto et al.

(10) Patent No.: US 10,562,024 B2
(45) Date of Patent: Feb. 18, 2020

(54) ELECTRONIC COMPONENTS ON PAPER-BASED SUBSTRATES

(75) Inventors: Fiorenzo Omenetto, Lexington, MA (US); David L. Kaplan, Concord, MA (US); Hu Tao, Medford, MA (US)

(73) Assignee: Tufts University, Medford, MA (US)

( * ) Notice: Subject to any disclaimer, the term of this patent is extended or adjusted under 35 U.S.C. 154(b) by 211 days.

(21) Appl. No.: 13/977,233

(22) PCT Filed: Jan. 4, 2012

(86) PCT No.: PCT/US2012/020244
§ 371 (c)(1),
(2), (4) Date: Feb. 19, 2014

(87) PCT Pub. No.: WO2012/094436
PCT Pub. Date: Jul. 12, 2012

(65) Prior Publication Data
US 2014/0154788 A1  Jun. 5, 2014

Related U.S. Application Data

(60) Provisional application No. 61/429,562, filed on Jan. 4, 2011.

(51) Int. Cl.
*B01L 3/00*       (2006.01)
*C12Q 1/54*       (2006.01)
*G01J 1/02*       (2006.01)
*G01J 5/02*       (2006.01)
*G01N 22/00*      (2006.01)

(52) U.S. Cl.
CPC .......... *B01L 3/502707* (2013.01); *C12Q 1/54* (2013.01); *G01J 1/02* (2013.01); *G01J 5/02* (2013.01); *G01N 22/00* (2013.01)

(58) Field of Classification Search
CPC .............. B01L 3/502707; G01N 22/00; G01N 21/3563; G01N 21/3581; G01J 5/02; G01J 1/02; C12Q 1/54
See application file for complete search history.

(56) References Cited

U.S. PATENT DOCUMENTS

| | | | |
|---|---|---|---|
| 5,420,016 A * | 5/1995 | Boguslaski et al. | ............ 435/12 |
| 6,933,112 B1 * | 8/2005 | Drewes et al. | ............... 435/6.11 |
| 7,381,955 B2 * | 6/2008 | Watanabe | .......... G01N 21/3581 |
| | | | 250/341.8 |
| 8,666,471 B2 | 3/2014 | Rogers et al. | |

(Continued)

FOREIGN PATENT DOCUMENTS

| WO | WO-99/54842 A1 | 10/1999 |
|---|---|---|
| WO | WO-2007/006833 A2 | 1/2007 |
| WO | WO-2011/115643 A1 | 9/2011 |

OTHER PUBLICATIONS

"Geometric." Merriam-Webster.com. Merriam-Webster, n.d. Web. Jan. 9, 2018.*

(Continued)

*Primary Examiner* — Melanie Brown
(74) *Attorney, Agent, or Firm* — Quarles & Brady, LLP

(57) ABSTRACT

The present disclosure relates to paper-based substrates and apparatus comprising such substrates. The apparatus may include a patterned conductive structure coupled to the paper-based substrate, wherein the patterned conductive structure responds to electromagnetic radiation.

30 Claims, 7 Drawing Sheets

(56) References Cited

U.S. PATENT DOCUMENTS

| | | | |
|---|---|---|---|
| 2005/0168339 A1 | 8/2005 | Arai et al. | |
| 2006/0231625 A1* | 10/2006 | Cumming et al. | 235/454 |
| 2006/0252065 A1* | 11/2006 | Zhao | B82Y 5/00 435/6.11 |
| 2009/0183989 A1* | 7/2009 | Yang et al. | 204/456 |
| 2010/0059597 A1 | 3/2010 | Iyengar et al. | |
| 2012/0184451 A1* | 7/2012 | Singamaneni | B82Y 5/00 506/9 |

OTHER PUBLICATIONS

"Pattern." Merriam-Webster.com. Merriam-Webster, n.d. Web. Jan. 9, 2018.*
Clark et al., Plasmonic Split-Ring Resonators as Dichroic Nanophotonic DNA Biosensors, JACS, vol. 131, pp. 17615-17619. (Year: 2009).*
Abe, K. et al., Inkjet-printed microfluidic multianalyte chemical sensing paper, Anal. Chem., 80(18):6928-34 (2008).
Barber, J. et al., Temperature-dependent far-infrared spectra of single crystals of high explosives using terahertz time-domain spectroscopy, J. Phys. Chem. A., 109(15):3501-5 (2005).
Bingham, C.M. et al, Planar wallpaper group metamaterials for novel terahertz applications, Opt. Express, 16(23):18565-75 (2008).
Bruzewicz, D.A. et al., Low-cost printing of poly(dimethylsiloxane) barriers to define microchannels in paper, Anal. Chem., 80(9):3387-92 (2008).
Calvert, P., Inkjet Printing for Materials and Devices, Chem. Mater., 13:3299-3305 (2001).
Chin, C.D. et al., Lab-on-a-chip devices for global health: past studies and future opportunities, Lab on a Chip, 7(1):41-57 (2007).
Chow, A.W., Lab-on-a-chip: Opportunities for Chemical Engineering, AIChE J., 48(8):1590-1595 (2002).
Dungchai, W. et al., Electrochemical detection for paper-based microfluidics, Anal. Chem., 81(14):5821-6 (2009).
Escarpa, A. et al., CE microchips: an opened gate to food analysis. Electrophoresis, 28(6):1002-11 (2007).
Figeys, D. and Pinto, D., Lab-on-a-chip: a revolution in biological and medical sciences, Anal. Chem., 72(9):330A-335A (2000).
Gardeniers, J.G. and Van Den Berg, A., Lab-on-a-chip systems for biomedical and environmental monitoring, Anal. Bioanal. Chem., 378(7)1700-3 (2004).
Hones, J., The Technology Behind Glucose Meters: Test Strips, Diabetes Technol. and Ther., 10( Supplement 1):S10-S26 (2008).
International Search Report for PCT/US2012/020244, 4 pages (dated Jul. 20, 2012).
Lim, D.V. et al, Current and developing technologies for monitoring agents of bioterrorism and biowarfare, Clin. Microbiol. Rev., 18(4):583-607 (2005).
Mabey, D. et al., Diagnostics for the developing world, Nat. Rev. Microbiol., 2(3):231-40 (2004).
MacGillivray, I. and Tovey, J.E., A study of the serum protein changes in pregnancy and toxaemia, using paper strip electrophoresis, J. Obstet. Gynaecol. Br. Emp., 64(3):361-4 (1957).
Martinez, A.W. et al., Patterned paper as a platform for inexpensive, low-volume, portable bioassays, Angew. Chem. Int. Ed. Engl., 46(8):1318-20 (2007).
Martinez, A.W. et al., Simple telemedicine for developing regions: camera phones and paper-based microfluidic devices for real-time, off-site diagnosis, Anal. Chem., 80(10):3699-707 (2008).
Moon, H. et al., An integrated digital microfluidic chip for multiplexed proteomic sample preparation and analysis by MALDI-MS, Lab Chip, 6(9)1213-9 (2006).
O'Hara, J.F. et al., Thin-film sensing with planar terahertz metamaterials: sensitivity and limitations, Opt. Express, 16(3):1786-95 (2008).
Padilla, W.J. et al., Electrically resonant terahertz metamaterials: Theoretical and experimental investigations, Phys. Rev. B, 75:041102(R) (2007).
Padilla, W.J. et al., Negative refractive index materials, Materials Today, 9(7-8):28-34 2006.
Preradovic, S. et al., Multiresonator-based chipless RFID system for low-cost item tracking, IEEE T. Microw. Theory, 57(5):1411-1419 (2009).
Smith, D.R. et al., Composite medium with simultaneously negative permeability and permittivity, Phys. Rev. Lett., 84(18):4184-7 (2000).
Tao, H. et al., Terahertz metamaterials on free-standing highly-flexible polyimide substrates, J. Phys. D: Appl. Phys., 41:232004 (2008).
Whitesides, G.M., The origins and the future of microfluidics, Nature, 442(7101):368-73 (2006).
Written Opinion for PCT/US2012/020244, 4 pages (dated Jul. 20, 2012).
Yager, P. et al., Microfluidic diagnostic technologies for global public health, Nature, 442(7101):412-8 (2006).
Yue, F. et al., A novel paper pH sensor based on polypyrrole, Sensor. Actuat. B. Chem., 32(1):33-39 (1996).
Zhao, W. and Van Der Berg, A., Lab on paper, Lab Chip, 8(12):1988-91 (2008).
Oosterbroek, E and Van Den Berg, A., Miniaturized Systems for (Bio)chemical Analysis and Synthesis, Lab-on-a-Chip, Elsevier Science (2003).

* cited by examiner

ELECTRONIC COMPONENTS ON PAPER-BASED SUBSTRATES

RELATED APPLICATIONS

This application is a 35 U.S.C. § 371 National Stage of International Application No. PCT/US12/20244, entitled "ELECTRONIC COMPONENTS ON PAPER-BASED SUBSTRATES" filed Jan. 4, 2012, which claims the benefit of and priority to U.S. Provisional Application No. 61/429, 562, entitled "PAPER-BASED METAMATERIALS" and filed Jan. 4, 2011, the contents of which are hereby incorporated by reference in their entirety.

GOVERNMENT SUPPORT

This invention was made with government support under grant 0802036 awarded by the National Science Foundation, grant W911NF-06-2-0040 awarded by the United States Army, and grant HR0011-08-1-0044 awarded by the Department of Defense. The government has certain rights in the invention.

BACKGROUND

Electronic components are conventionally fabricated on silicon substrates. Fabrication techniques for manufacturing silicon substrates can be time-consuming and/or costly.

SUMMARY

Among other things, the present invention encompasses the recognition that electronic components can be fabricated on paper-based substrates. Fabricating electronic components on paper-based substrates can transform the paper-based substrates into devices (e.g., sensors). Electronic components on paper-based substrates may exhibit desirable properties (e.g., sensitivity, targeted electromagnetic behaviors). The properties of electronic components on paper-based substrates may be comparable to properties of electronic components on alternative substrates. Since paper-based substrates can be inexpensive to produce and/or obtain, devices fabricated using paper-based substrates can achieve significant cost savings over conventional alternative substrates.

Paper-based substrates can be fabricated and/or altered to introduce additional functionality to the device. According to the present invention, one or more dopants can be incorporated into a paper-based substrate and/or applied to a surface of a paper-based substrate. The dopant(s) can influence the properties of electronic components. For example, dopant(s) can influence the properties of electronic components during exposure to environments that may include other substances to be detected. Thus, the dopants can introduce additional functionality into sensors, among other devices.

In some aspects, the present disclosure is directed to an apparatus, which may comprise a paper-based substrate. The apparatus may include a patterned conductive structure coupled to the paper-based substrate, wherein the patterned conductive structure responds to electromagnetic radiation. The paper-based substrate may have a surface roughness greater than 10 nm, e.g., about 11 nm, about 12 nm, about 13 nm, about 14 nm, about 15 nm, about 16 nm, about 17 nm, about 18 nm, about 19 nm, about 20 nm, or greater. The paper-based substrate may have a surface roughness of about 16 nm.

The paper-based substrate may include wood pulp. The paper-based substrate may include a dopant, such as a biological element. The dopant may be a pharmaceutical, antibody, fragment or portion of an antibody, antibiotic, enzyme, organic indicator, photoactive dye, cell, protein, peptide, nucleic acid analogue, nucleotide, oligonucleotide, peptide nucleic acid, aptamer, hormone, hormone antagonist, growth factor, fragment of a growth factor, variant of a growth factor, recombinant growth factor, fragment of a recombinant growth factor, variant of a recombinant growth factor, cytokine, antimicrobial compound, virus, antiviral, toxin, prodrug, drug, chemotherapeutic agent, small molecule, chromophore, light-emitting organic compound, light-emitting inorganic compounds, light-harvesting compound, light-capturing complex, or combinations thereof. The dopant may modulate the electromagnetic radiation.

The patterned conductive structure may be disposed on a surface of the paper-based substrate. The patterned conductive structure may be embedded in the paper-based substrate. The patterned conductive structure may include a conductive material. The conductive material may include gold, aluminum, chromium, silver, platinum, copper, titanium, nickel, rhodium, cobalt, magnesium, iron, zirconium, molybdenum, palladium, hafnium, iridium, tungsten, tantalum, indium tin oxide (ITO), polysilicon, graphite, or any combination thereof. The patterned conductive structure may include a resonator, split-ring resonator, polarization-sensitive electric resonator, polarization non-sensitive electric resonator, radio-frequency identification (RFID) device, metamaterial structure, antenna, conductive coil, or any combination thereof.

The apparatus may respond to microwave radiation, infrared radiation, visible radiation, ultraviolet radiation, or any combination thereof. The apparatus may respond to the electromagnetic radiation to exhibit an electromagnetic signature in the terahertz (THz) frequencies, megahertz (MHz) frequencies, gigahertz (GHz) frequencies, petahertz (PHz) frequencies, or any combination thereof. The apparatus may respond to the electromagnetic radiation to exhibit an electromagnetic signature, the electromagnetic signature comprising a resonance response. The apparatus may modulate the electromagnetic radiation.

In some aspects, the present disclosure is directed to a method. The method may include positioning a shadow mask on a paper-based substrate. The method may include depositing a conductive material on the paper-based substrate through openings in the shadow mask. The method may include removing the shadow mask from the paper-based substrate. Depositing the conductive material may include spray-depositing the conductive material. Depositing the conductive material may include evaporating the conductive material through the openings in the shadow mask.

BRIEF DESCRIPTION OF THE DRAWING

The foregoing and other objects, aspects, features, and advantages of the disclosure will become more apparent and better understood by referring to the following description taken in conjunction with the accompanying drawings, in which.

Figure 1:
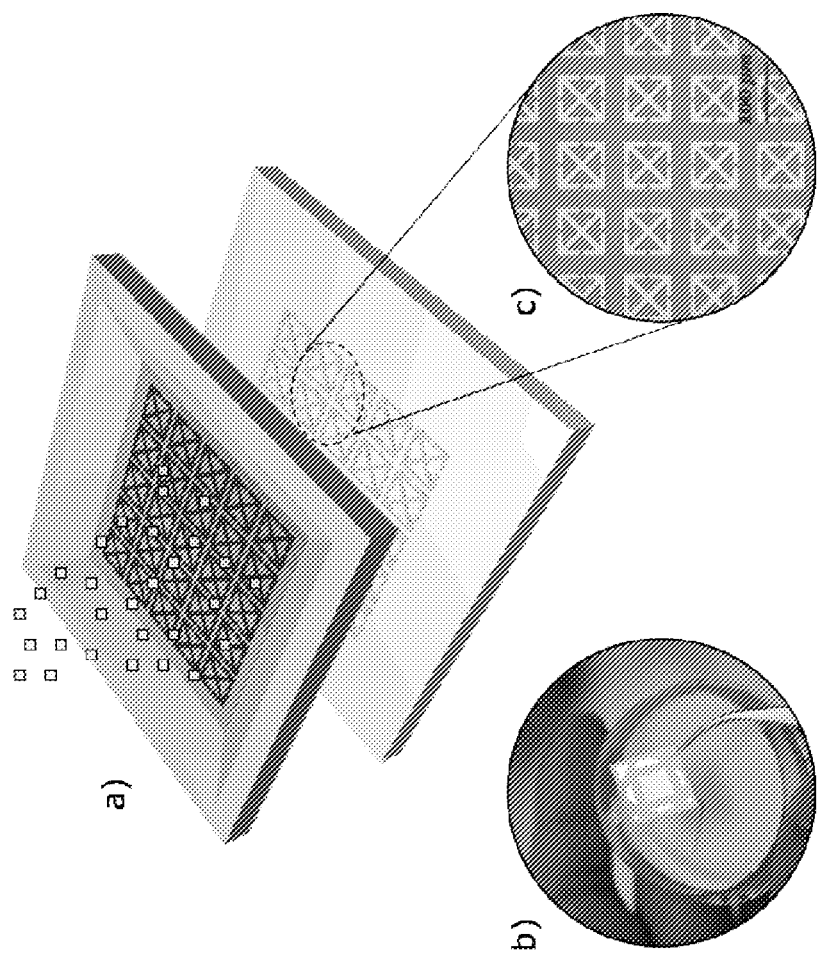
FIG. 1A depicts a schematic of micrometer-sized metamaterial resonators fabricated on paper-based substrates with a pre-defined micro stencil.
FIG. 1B depicts a terahertz metamaterial fabricated on a paper-based substrate.
FIG. 1C depicts an optical microscopy image of metamaterials fabricated on a paper-based substrate.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF CERTAIN EMBODIMENTS

Among other things, the present disclosure relates to electronic components fabricated on paper-based substrates and methods for fabricating the electronic components on the paper-based substrates. In the broadest sense, the present disclosure relates to electronic components deposited upon or incorporated into a variety of paper media as substrates. In some embodiments, already existing paper materials can be used or reused/recycled for fabricating the paper-based substrates as described in the present application. The manufacture of such products can therefore be cost-effective, as compared to conventional electronic components and metamaterials. In some embodiments, paper-based substrates and/or paper-based electronic components described herein are intended as one-time-use, or disposable products.

Fabricating electronic components on paper-based substrates can transform the paper-based substrates into useful devices. Electronic components described herein are typically of a nano- to micro-meter scale. As described in more detail below, the degree of resolution which can be achieved in a particular device depends in part on the ability of a fabrication technique to substantially preserve the integrity (e.g., avoid distortion, degradation) of the paper-based substrate while fabricating electronic components thereon. Electronic components on paper-based substrates may exhibit desirable properties (e.g., sensitivity, targeted electromagnetic behaviors). The properties of electronic components on paper-based substrates may be comparable to properties of electronic components on alternative substrates. Since paper-based substrates can be inexpensive to produce and/or obtain (e.g., easily accessible), devices fabricated using paper-based substrates can achieve significant cost savings over alternative substrates.

Paper-based substrates can be fabricated and/or altered to introduce additional functionality to the device. For example, one or more dopants can be incorporated into a paper-based substrate and/or applied onto a surface of a paper-based substrate. As used herein, the term dopant refers broadly to an agent or additive that may be added to paper-based substrates or paper-based electronic components. In some embodiments, the dopant(s) can influence the properties of electronic components. For example, the dopant(s) may alter the electromagnetic response of the electronic components. In some embodiments, when electronic components are placed in an environment with a target substance for detection (e.g., toxin, glucose), the dopant(s) and the target substance for detection may jointly influence the properties of the electronic components. For example, the dopant(s) and target substance may jointly alter the electromagnetic response of the electronic components. Thus, the dopants can introduce additional functionality into sensors, among other devices. In some embodiments, dopants may enable the creation of sensors that can monitor environments for target substances.

Inexpensive paper-based sensing kits (e.g., test strips) have been playing an important role in a variety of ready-to-use diagnostics. The inclusion of easily patterned resonant electromagnetic structures adds considerable utility to the platform in support of an increasing number of applications. Though the paper-based metamaterials were designed to be functional at THz frequencies where many materials such as volatile chemicals and DNA exhibit unique electromagnetic fingerprints [27], it can be readily extended to other regions of the electromagnetic spectrum by simply scaling the SRR sizes and utilizing appropriately matched readout systems. Additionally, besides acting as an agile sensor, the natural narrow band metamaterial resonance is a salient feature for identification and tracking applications by embedding the sub-wavelength metamaterial resonator(s) in the documents, such as shipping labels, passports, and currency bills, which will show tremendous power with the facilitation from well developed RFID [28] and ink-jet technologies [29].

Overview of Electronic Components Fabricated on Paper-Based Substrates

In some embodiments, a paper-based substrate can support one or more patterned conductive structures. The one or more patterned conductive structures may be an electronic component. The combination of the paper-based substrate and patterned conductive structure can exhibit a unique electromagnetic signature. Many factors can influence the electromagnetic signature. Exemplary factors include, but are not limited to, the geometry of the patterned conductive structure, dielectric properties of the patterned conductive structure and/or paper-based substrate, and dopants coupled to the paper-based substrate (e.g., embedded within the paper-based substrated, applied to a surface of the substrate).

In some embodiments, a patterned conductive structure can respond to electromagnetic radiation at a desired wavelength or range of wavelengths. Exemplary wavelengths include microwave, infrared, visible, and/or ultraviolet wavelengths. In response to the radiation, a patterned conductive structure can exhibit an electromagnetic signature at a targeted frequency or range of frequencies. In some embodiments, the electromagnetic signature can exhibit notable features (e.g., peaks, troughs, known patterns involving peaks and troughs) at terahertz (THz), megahertz (MHz), and/or petahertz (PHz) frequencies. The electromagnetic signature can include a resonant electromagnetic response. The response can include the amplitude and phase of the transmission, reflection, and/or absorption of electromagnetic radiation at various frequencies, including the resonance frequency.

In some embodiments, at least one dimension of a patterned conductive structure can be as small as or smaller than a wavelength of incident electromagnetic radiation. For example, for visible light with wavelengths shorter than one micrometer (e.g., 560 nanometers for sunlight), a dimension of a patterned conductive structures can be less than the 560 nanometers, or even 280 nanometers. For microwave radiation, dimensions of a patterned conductive structure can be on the order of one decimeter.

In some embodiments, a patterned conductive structure can respond to electromagnetic radiation according to the structure's geometric scale. In some embodiments, a patterned conductive structure can respond to infrared radiation. When the structure is geometrically scaled, the scaled structure can respond to microwave or ultraviolet radiation, instead of infrared radiation. In some embodiments, a structure geometrically scaled to be smaller can response to shorter wavelengths of electromagnetic radiation. For example, a patterned conductive structure can be on the order of a wavelength or half-wavelength of incident electromagnetic radiation. In some embodiments, patterned conductive structures of about 400 nm respond to visible radiation. In some embodiments, patterned conductive structures of about 1 μm respond to infrared radiation.

In some embodiments, patterned conductive structures (e.g., resonators) can be conduits for resonant electromagnetic modes. For example, a 30 μm ring resonator can support THz modes. Ring resonators on the order of several cm can support GHz modes. Ring resonators on the order of tens of cm can support MHz modes.

In some embodiments, dopants in the paper-based substrate can change dielectric properties of the paper-based substrate and/or the patterned conductive structure. Thus, dopants can change the intensity and/or amplitude of transmitted, reflected, and/or absorbed electromagnetic radiation. An exemplary dopant is or comprises horseradish peroxidase (HRP). When a paper-based substrated embedded with HRP is exposed to teramethylbenzidine (TMB), the electromagnetic signature of patterned conductive structures on the doped paper-based substrate can shift to lower frequencies. The dopants can change the resonance frequency of the patterned conductive structures. In some embodiments, portions of the patterned conductive structures can be removed to alter the electromagnetic responses of the structures.

In some embodiments, the electromagnetic response of the patterned conductive structures can originate from oscillating electrons in the conductive material (e.g., metal). The oscillations can permit the design of a specific resonant response according to the electrical permittivity ($\epsilon$) or magnetic permeability ($\mu$) of the patterned conductive structure.

In some embodiments, a resonator, such as an SRR, can exhibit a resonant magnetic or electric response to achieve an effective negative permeability ($\mu$) at a frequency range above the resonance frequency. A resonator can exhibit a resonant response to the electric component of a light field when the electric field is aligned perpendicular to the resonator gap to excite the circulating currents within the resonator, resulting in effective negative permittivity ($\epsilon$).

In some embodiments, an SRR can be modeled as a LC resonator (i.e., a resonant circuit with an inductor and a capacitor). The resonance frequency of the SRR can be represented as $\omega_0 \sim \sqrt{1/LC}$, wherein the inductance can result from the current path of the SRR and capacitance can be determined by the split gap and the dielectric properties of the paper-based substrate and other elements in the gap. A change in the capacitance or inductance can change the SRR's resonant response. As an SRR can be sensitive to its environment, an SRR can be suitable for integration into devices for sensing and detecting applications.

In some embodiments, metamaterials are sub-wavelength composites which gain their properties from structure rather than composition. The EM response originates from oscillating electrons in highly conducting metals such as gold or copper, allowing for a designed, programmable resonant response [19]. While most paper-based biosensors use colorimetric readout and detect the color or intensity change in visible range, metamaterials offer a broader operating range, covering from radiofrequency to optical wavelengths [20]. Split ring resonators (SRRs) are the most commonly used elements to build MM structures and devices. The resonant response of SRRs can be easily understood using a LC circuit model and SRR can be equivalently regarded as an LC resonator with a resonance frequency of $\omega_0 \sim \sqrt{1/LC}$, where the inductance (L), results from the current path of the SRR and the capacitance (C) is determined by the split gap and the dielectric properties of the substrate and the matter that fills in the gap. Patterning metamaterials on paper substrates yields an suitable candidate for a platform where the resonance shifts, mainly due to alterations in the SRR capacitance induced by the added analyte [21], can be utilized for quantitative biochemical sensing applications.

In some embodiments, the electromagnetic signature can change when a change occurs in the dielectric constant of the paper-based substrate, the paper-based substrate with dopants, and/or the patterned conductive structure. Such a change can be induced by chemical, biochemical, or other environmental factors, such as temperature, mechanical strain, gas concentration, gas release, chemical reactions (e.g., surface reactions, bulk reactions), hydration, and/or material removal.

In some embodiments, a change can shift the resonance frequency of the electromagnetic signature to another frequency. For example, the change can shift the resonance frequency to higher or lower frequencies. In some embodiments, a change can modulate the amplitude of the resonant response of the electromagnetic signature. In some embodiments, a change can shift the resonance frequency and modulate the amplitude of the resonant response of the electromagnetic signature. In some embodiments, the change can alter the width of a feature of the electromagnetic signature (e.g., the full width at half maximum of the spectral response).

By controlling the geometry of patterned conductive structures, the dopants in the paper-based substrate, or various other factors, a user can design a paper-based substrate with patterned conductive structures that exhibits desired electromagnetic responses at target frequencies. In some embodiments, the user can design a paper-based substrate with patterned conductive structures that exhibits desired electromagnetic responses at target frequencies in response to an environmental factor.

In some embodiments, an electronic component fabricated on a paper-based substrate can have resonant sub-wavelength magnetic properties that comprises one or more layers of metamaterial or patterned structure made of conductive material (e.g., metal) and a paper-based substrate that carries the one or more layers of metamaterial or patterned structure made of conductive material (e.g., metal) on the substrate.

In some embodiments, a resonant electromagnetic structure comprising an array of metamaterial components may be fabricated on a paper-based substrate. The resonant electromagnetic structure of the electronic components may be constructed to modulate the electromagnetic radiation. The electronic components may be disposed on or embedded in the paper-based substrate. At least some of the metamaterial elements are smaller than the wavelength of the electromagnetic radiation for inducing subwavelength resonant electromagnetic response.

In some embodiments, electronic components fabricated on paper-based substrates can operate at teraherz (THz, 1 THz=1012 Hz) frequencies. The THz region of the electromagnetic spectrum can have the potential for applications ranging from spectroscopic imaging to short-range secure communication. Naturally occurring materials, however, typically do not have the appropriate response at THz frequencies. Thus, to date, important THz components and devices such as switches, modulators, and phase shifters, have not been readily available in nature. Appropriate components and devices remain to be explored for the generation, detection, and spatial and temporal control of THz radiation to realize the applications in THz regime. By further extending the material design implemented in THz frequencies, the designed components and devices would be applicable at a broader wavelength regime. In certain embodiments, the present disclosure is directed to THz components comprising a paper-based substrate and an electronic component.

Electronic components provided in accordance with the present disclosure can comprise an array of metamaterial elements disposed on or embedded in a paper-based substrate, forming a resonant electromagnetic structure that modulates an electromagnetic radiation at a wide range of frequencies, including terahertz regime. A simple methodology is provided herein to directly spray large-area metamaterial structures on a paper-based substrate, resulting in a device with a resonant electromagnetic structure that exhibits strong resonances at desired frequencies. Such an electronic component can modulate an electromagnetic radiation at a wide range of electromagnetic spectrum including, but not limited to, a THz regime.

Exemplary Electronic Components

A patterned conductive structure can be a structure with a user-designed electromagnetic response. In some embodiments, the patterned conductive structure is or comprises a source, lens, switch, modulator, detector, or any combination thereof. In some embodiments, the patterned conductive structure is or comprises an antenna. In some embodiments, the patterned conductive structure is or comprises a radio-frequency identification (RFID) device. In some embodiments, the patterned conductive structure is or comprises a split-ring resonator (SRR). In some embodiments, the patterned conductive structure is or comprises a metamaterial structure.

In some embodiments, the patterned conductive structure is or comprises an electrode. In some embodiments, the patterned conductive structure is or comprises a passive electronic. In some embodiments, the patterned conductive structure is or comprises a thin film semiconductor component. In some embodiments, the patterned conductive structure is or comprises a solar cell. In some embodiments, the patterned conductive structure is or comprises a capacitor, inductor, or resistor.

In some embodiments, the patterned conductive structure is or comprises a light emitting diode (LED). In some embodiments, the patterned conductive structure is or comprises a transistor. In some embodiments, the patterned conductive structure is or comprises a conductive coil. In some embodiments, the patterned conductive structure is or comprises a coil that receives power. In some embodiments, the patterned conductive structure is or comprises a photodetector. In some embodiments, the patterned conductive structure is or comprises a vertical cavity surface emitting laser (VCSEL). In some embodiments, the patterned conductive structure is or comprises a thin-film electronic. In some embodiments, the patterned conductive structure is or comprises a resonator cavity.

In some embodiments, the patterned conductive structures comprise a layer of conductive material. In some embodiments, the patterned conductive structures comprise more than one layer of conductive material. The patterned conductive structures can have dimensions of any size. For example, dimensions of the patterned conductive structures can be on the order of micrometers or nanometers. Exemplary dimensions include structures that measure 10 µm×10 µm, 50 µm×50 µm, 100 µm×100 µm, 4 cm×4 cm, or 6 cm×6 cm in their entirety, although other dimensions may be used. In some embodiments, features of the patterned conductive structure can measure 200-500 nm along a dimension. In some embodiments, features of the patterned conductive structure can measure 200-500 nm along a dimension. Features of other sizes can be used.

The geometry of patterned conductive structures can be scaled to create a larger or smaller structure. For example, a pattern for a conductive structure can be scaled from an order of micrometers to an order of nanometers, or the reverse.

Exemplary Materials of Electronic Components

In some embodiments, an electronic component can include metal. In some embodiments, an electronic component can include a conductive metal. Exemplary metals can include, but are limited to, gold, copper, aluminum, silver, platinum, chromium, cobalt, nickel, rhodium, titanium, magnesium, iron, zirconium, molybdenum, palladium, hafnium, iridium, tungsten, tantalum, and combinations thereof. In some embodiments, an electronic component can include a non-metal. Exemplary non-metals can include indium tin oxide (ITO), polysilicon, graphite, and combinations thereof. In some embodiments, an electronic component can include a combination of one or more metals and one or more non-metals.

Exemplary Paper-Based Substrates

There is increasing interest in the development of cost-effective, practical, portable and disposable diagnostic devices suited to on-site detection and analysis applications, which hold great promise for global health care [1-2], environmental monitoring [3], water and food safety [4], as well as military and homeland security [5]. Lab-on-a-chip (LOC) devices, which scale single or multiple lab processes down to chip-format (only millimeters to a few square centimeters in size) facilitated by micro- and nano-scale technologies, have attracted significant attention because of their small sample volume requirements and excellent portability [6]. Various LOC devices have been designed and fabricated in the past two decades, most of which involve a lithography-based patterning process on a solid or elastomeric substrate, such as glass or plastic, for a variety of functionalities which include sample preparation [7], microfluidic mixing [8], bio-chemical reactions [9] and analysis [10].

Paper, a versatile material originating from ancient China, has recently reemerged as a highly promising candidate as the LOC substrate material [11-12]. Inexpensive and abundant, paper based biosensors could be more accessible to average users, particularly those in developing countries, where cost and ease of use are among the top priorities [13]. Additionally, as an environmentally friendly material, paper is largely sustainable and disposable, enabling it to stand out amongst its peers as a path to "green" sensors. Paper-based bioanalysis, which started in early 20th century and culminated with the Nobel Prize winning invention of a paper chromatography technique in 1952, has been widely used in our daily lives in devices such as pH paper [14] and pregnancy test strips [15]. These paper-based strip tests are advantageous in cases where only qualitative analysis is needed, and simplicity (and low cost) matters most. However, such devices are not sufficiently sensitive to certain biomarkers where a quantitative analysis is desired, as is the case for glucose and protein sensing. Progress on quantitative analysis using paper-based devices has been promising in the past 5 years, thanks to the new developments in micro- and nano-technologies. For example, Whitesides and colleagues have successfully developed microfluidics devices with millimeter-sized fluidic channels patterned on a paper [16-17]. By incorporating an imaging component into the system and monitoring the color intensity change induced by the analyte, these devices were able to detect glucose quantitatively [18]. Nonetheless, when compared with LOCs fabricated on conventional substrates, paper-based biosensors still need to improve sensitivity and accuracy, partially due to the difficulty to get distinctive patterning (such as small feature size and sharpness) on paper substrates where conventional photolithography techniques are difficult to apply.

In some embodiments, the paper-based substrate can be paper. The paper-based substrate can be newsprint. The paper-based substrate can be magazine print. The paper-based substrate can be photography paper. The paper-based substrate can be tissue. The paper-based substrate can be woven paper. The paper-based substrate can be gloss paper. The paper-based substrate can be wrapping paper, such as wax and kraft papers. The paper-based substrate can be writing paper, such as ledger, bank, and bond paper. The paper-based substrate can be blotting paper. The paper-based substrate can be drawing paper. Non-limiting examples of useful paper types include: Some paper types include: Bank paper, Banana paper, Bond paper, Book paper, Coated paper: glossy and matte surface, Construction paper/sugar paper, Cotton paper, Fish paper (vulcanized fibres for electrical insulation), Inkjet paper, Kraft paper, Laid paper, Leather paper, Mummy paper, Sandpaper, Tyvek paper, Wallpaper, Washi, Waterproof paper, Wax paper, Wove paper and Xuan paper.

The paper-based substrate can be tearable. The paper-based substrate can be adapted to receive a liquid substance disposed thereon. In some embodiments, the paper-based substrate may be porous and thus adapted to absorb one or more substances. In some embodiments, the paper-based substrate may include a coating. The coating can include calcium carbonate, china clay, or a combination thereof. In some embodiments, the coating can be polished (e.g., via calendaring).

In some embodiments, the paper-based substrate can include fibrous pulp. For example, the paper-based substrate can include cellulose pulp. The pulp can be derived from wood, rags, grasses, cotton, straw, bagasse, or any other organic matter in any combination. In some embodiments, the paper-based substrate can be a paper composite. For example, pulp can be blended with other substances to form a composite, and the composite can be processed into sheets of paper-based substrate.

In some embodiments, the paper-based substrate may have a surface roughness of at least 10.0 nm. In some embodiments, the paper-based substrate may have a surface roughness of at least 15.0 or at least 20.0 nm. In some embodiments, the thickness of the electronic components may be associated with the surface roughness of the paper-based substrates. As the surface roughness of the paper-based substrate increases, the thickness of the electronic components may be increased to ensure proper functionality of the components. For example, in some embodiments, electronic components fabricated on photography paper with a surface roughness of about 16 nm may require a metal layer of about 150 nm to exhibit the desired electromagnetic responses. In some embodiments, electronic components fabricated on printing paper with a surface roughness greater than 20 nm may require a metal layer greater than 150 nm (e.g., about 175 nm, about 200 nm).

Exemplary Dopants Used in Conjunction with the Paper-Based Substrate

In some embodiments, the paper-based substrate may include one or more dopants. The one or more dopants may be embedded in the paper-based substrate. For example, when paper is being fabricated, one or more dopants may be mixed into the pulp before the pulp is fed to a paper machine. One or more dopants may be mixed into pulp from recycled papers prior to feeding to a paper machine. In'some embodiments, the one or more dopants may be distributed throughout the pulp. In some embodiments, the one or more dopants may be distributed unevenly within the pulp. In some embodiments, uneven distribution of the one or more dopants may form a gradient within the pulp, and ultimately, the paper. In some embodiments, one or more dopants may be localized to one or more portions within the pulp, and ultimately, the paper.

In some embodiments, the one or more dopants may be applied to a surface of the paper-based substrate. For example, a dopant may be sprayed on a surface of the paper-based substrate. The dopant may be evaporated onto the surface of the paper-based substrate. The dopant may be painted onto a surface of the paper-based substrate. The dopant may be poured onto a surface of the paper-based substrate. The paper-based substrate may be dipped in a solution containing the dopant.

Exemplary dopants may be polymer elements. In some embodiments, a polymer element is or comprises a biological polymer (e.g., a peptide and nucleic acid). In some embodiments, a polymer element does not comprise, or does not include, a biological polymer. In some embodiments, a dopant may be at least one polypeptide or protein. In some embodiments, a dopant may be at least one enzyme. In some embodiments, a dopant may be at least one antibody or antigen-binding fragment thereof. In some embodiments, a dopant may be at least one pharmacologic agent.

In some embodiments, a dopant may be at least one active agent (e.g., biologically active agent). The variety of active agents that can be used in conjunction with the paper-based substrate is vast. For example, useful active agent may be a therapeutic agent or biological material, such as cells, proteins, peptides, nucleic acid analogues, nucleotides, oligonucleotides, nucleic acids (DNA, RNA, siRNA, etc.), peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, anti-inflammation agent, antifungals, antivirals, toxins, prodrugs, chemotherapeutic agents, small molecules, drugs (e.g., drugs, dyes, amino acids, vitamins, antioxidants) and combinations thereof.

Exemplary antibiotics suitable for inclusion in the paper-based substrate include, but are not limited to: aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, and fusidic acid.

Exemplary dopants suitable for use herein include, but are not limited to: progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

Exemplary antibodies include, but are not limited to: abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, the paper-based substrate may include a polypeptide (e.g., protein), including but are not limited to: one or more antigens, cytokines, hormones, chemokines, enzymes, and any combination thereof.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

Additional or alternative active agents suitable for use herein include cell growth media, such as Dulbecco's Modified Eagle Medium, fetal bovine serum, non-essential amino acids and antibiotics; growth and morphogenic factors such as fibroblast growth factor, transforming growth factors, vascular endothelial growth factor, epidermal growth factor, platelet derived growth factor, insulin-like growth factors), bone morphogenetic growth factors, bone morphogenetic-like proteins, transforming growth factors, nerve growth factors, and related proteins (growth factors are known in the art, see, e.g., Rosen & Thies, CELLULAR & MOLECULAR BASIS BONE FORMATION & REPAIR (R.G. Landes Co., Austin, Tex., 1995)); anti-angiogenic proteins such as endostatin, and other naturally derived or genetically engineered proteins; polysaccharides, glycoproteins, or lipoproteins; anti-infectives such as antibiotics and antiviral agents, chemotherapeutic agents (i.e., anticancer agents), anti-rejection agents, analgesics and analgesic combinations, anti-inflammatory agents, and steroids.

In some embodiments, an active agent may be an organism such as a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

An active agent for use in the paper-based substrate may be an optically and/or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

Methods of Fabricating Electronic Components on Paper-Based Substrates

While conventional tests use a strip of paper doped with an antibody specific to an antigen of interest, patterned papers offer more opportunities for multiplex and quantitative analysis [22]. However, while porosity is a key feature in making paper a favorable material for diagnosis applications, achieving well defined patterns on porous paper substrates with high resolution (e.g. few micrometers) remains a challenge. This is mainly due to the inability to use conventional photolithography based micro-fabrication techniques where chemical solutions are generally used. Paper can be easily distorted and degraded during the solvent rinses used in these processes and alternative fabrication techniques have yet to be explored. A shadow mask patterning fabrication process can be used. Patterning can be based on selective deposition of a target material (gold in the present case) through a 500 nm thick silicon nitride (SiNx) films micro stencil-based shadow mask Patterned conductive structures can be disposed on a paper-based substrate according to many fabrication techniques. For example, a patterned conductive structure can be spray-deposited on a surface of a paper-based substrate. In another example, a patterned conductive structure can be transferred by contact from another substrate to a surface of a paper-based substrate. In some embodiments, a patterned conductive structure can be embedded in a paper-based substrate. For example, a patterned conductive structure can be formed on a another substrate, and a paper pulp can be disposed on the substrate. As the paper pulp dries, the paper pulp can assemble around the patterned conductive structure, thereby embedding the conductive material (e.g., metal) within the paper.

In some embodiments, the patterned conductive structures can be formed by spray deposition. A shadow mask can be attached to the paper-based substrate. In some embodiments, the shadow mask can be accurately positioned and/or fixed relative to the paper-based substrate via alignment under microscopy. In some embodiments, the shadow mask can be contact-positioned on a paper-based substrate, e.g., the shadow mask can be placed in contact with the paper-based substrate and aligned and/or positioned without use of adhesives. In some embodiments, clamps and/or clips can secure contact between the shadow mask and the paper-based substrate. In some embodiments, the edges of the shadow mask can be attached to the paper-based substrate with tapes, by way of example.

A conductive material can be spray-deposited on the paper-based substrate through the shadow mask, thereby forming a patterned conductive structure or an array of patterned conductive structures. The shadow mask can provide a predetermined geometry (e.g., structural features, patterns for the array) for the patterned conductive structures. After the conductive material is applied, in some embodiments, the shadow mask can be removed without use of solvents or other treatments. For example, clamps and/or clips can be removed from the shadow mask and paper-based substrate. The shadow mask can be manually separated from the paper-based substrate. In some embodiments, the shadow mask can be removed by peeling off tape that attaches the shadow mask to the paper-based substrate.

In some embodiments, the shadow mask can be a stencil (e.g., a large area stencil, micro-stencil, nano-stencil). In some embodiments, the deposition can be used in combination with soft fabrication techniques (e.g., elastomeric stamps, molds, conformable photomasks).

In some embodiments, the patterned conductive structures can be formed on a paper-based substrate via various lithography processes. Such lithography processes can include processes commonly applied to substrates, such as silicon. Exemplary lithography processes include nanoimprint lithography, optical lithography (e.g., water-based optical lithography), plasma etching, and laser machining. In some embodiments, the patterned conductive structures can be formed on a paper-based substrate via various printing processes. Exemplary printing processes include microfluidic printing, inkjet printing, laser printing, and thermal printing, although other printing techniques can be used.

In any of these embodiments, the process for forming patterned conductive structures can be adapted to create structures that response to electromagnetic radiation at different wavelengths, e.g., microwave radiation, visible radiation. For example, electron-beam writing can be used to fabricate smaller features down to tens of nanometers. In some embodiments, patterns on the micro-stencils can be scaled to create nano stencils.

Electronic components fabricated on paper-based substrates can be used in novel applications such as sensors, labels, identifiers, and explosives detection, among others.

In some embodiments, electronic components fabricated on a paper-based substrate can be used as a biological and/or chemical analyte sensor. A biological and/or chemical analyte can interact with a dopant incorporated into or applied onto a paper-based substrate. The resonance frequency or resonance strength and/or amplitude of the changed electromagnetic signature can indicate the presence of the analyte.

In some embodiments, patterned conductive structure fabricated onto a paper-based substrate can be used for tracking. For example, a patterned conductive structure can be an antenna with an RFID electromagnetic signature. Paper-based substrates with antennae can be adhered to any object, such as packaging, food, pills, inventory, etc. The antennae can operate at various frequencies, such as MHz, GHz, or THz. The antennae can be scanned and information contained on the antennae can be entered into a database. Thus, the locations of objects associated with scanned antennae can be recorded.

In some embodiments, a paper-based substrate with a patterned conductive structure can be used as a sensor. The paper-based substrate and structure can be designed such that their interactions with a predetermined chemical cause the patterned conductive structure to exhibit a predetermined electromagnetic signature. For example, a paper-based substrate with a patterned conductive structure can be laid under produce, meat, or any other organic matter. As the organic matter spoils, dopants applied to a surface of the paper-based substrate can interact with the ethylene released from organic matter to shift the electromagnetic signature of the patterned conductive structure to a predetermined frequency. In another example, dopants applied to a surface of the paper-based substrate can interact with bacteria (e.g., *e-coli, salmonella, listeria, shigella*) to shift the electromagnetic signature of the patterned conductive structure. Users can detect this shift to determine the food has spoiled or been contaminated.

A paper-based substrate with a patterned conductive structure can be designed to detect glucose. A user can place a drop of blood on the patterned conductive structure, and the level of glucose in the blood can change the electromagnetic signature of the structure. A device can scan and interpret the electromagnetic signature to determine the level of glucose in the user's blood.

The patterned conductive structures resonant at terahertz frequencies can be used for identification and bio-sensing, as numerous chemical and biological agents show unique "fingerprints" at the THz range.

In some embodiments, a patterned conductive structure can be fabricated on a paper to transform the paper into a technical device. For example, a patterned conductive structure can be spray deposited onto a page of a passport. In some embodiments, the electromagnetic signature of the patterned conductive structure may be altered in the presence of a substance used to create explosives. A user may compare the electromagnetic signature of the patterned conductive structure with the signature of a structure in a controlled environment (e.g., a reference signature) to determine if the paper has been exposed to the substances.

In some examples, a patterned conductive structure can be spray deposited onto an envelope that has been passed through a post office. In some embodiments, the electromagnetic signature of the patterned conductive structure may be altered in the presence of a toxin, such as anthrax. A user may compare the electromagnetic signature of the patterned conductive structure with the signature of a structure in a controlled environment (e.g., a reference signature) to determine if the envelope has been exposed to anthrax.

In some examples, a patterned conductive structure can be printed onto a test probe (such as test strip or filter) to be placed in high traffic, public locations, or other areas suitable for environmental sampling for collecting and monitoring air samples, water samples, soil samples, etc. In some embodiments, the electromagnetic signature of the patterned conductive structure may be altered in the presence of a bioterrorism agent. In some examples, a bioterrorism agent may be Bacterial Bio-agents (e.g., *Bacillus anthracis, Brucella abortus, Brucella melitensis, Brucella suis, Vibrio cholerae, Corynebacterium diphtheriae, Shigella dysenteriae, Escherichia coli, Burkholderia mallei, Listeria monocytogenes, Burkholderia pseudomallei, Yersinia pestis*, and *Francisella tularensis*); Chlamydial Bio-agents (e.g., *Chlamydophila psittaci*); Rickettsial Bio-agents (e.g., *Coxiella* burnetii, Rickettsia rickettsii, Rickettsia prowazekii, and Rickettsia typhi); Viral Bio-agents (e.g., Eastern equine encephalitis virus, Venezuelan Equine Encephalomyelitis virus, Western equine encephalitis virus, Japanese encephalitis virus, Rift Valley fever virus, Variola virus, Yellow fever virus); Mycotic Bio-agents (e.g., Coccidioides immitis Biological Toxins, Botulinum toxins, *Ricin, Saxitoxin, Staphyloccocal enterotoxin* B, *Tetrodotoxin*, and *Trichothecene mycotoxins*); and Biological Vectors (e.g., Malaria, Dengue fever, Yellow fever, other Arboviruses, Plague, and Murine typhus). A user may compare the electromagnetic signature of the patterned conductive structure with the signature of a structure in a controlled environment (e.g., a reference signature) to determine if the test strip has been exposed to a bioterrorism agent.

In some embodiments, electronic components fabricated on paper-based substrates can be packaged into kits. The paper-based substrates can be cut into strips for a package. In some embodiments, the paper-based substrates with electronic components can be transformed into assay strips for the kit. In some embodiments, the kit can include an instrument to measure the electromagnetic response of the electronic components on a strip. In some embodiments, the kit can include swabs for obtaining a sample of material for testing.

In some embodiments, the kit can include an instruction manual with instructions for applying a strip to a sample (e.g., dipping the strip in a solution for a predetermined period of time, exposing the strip to an environment for a predetermined period of time, swabbing a test location and applying the swab to the strip for a predetermined period of time). The instruction manual can include instructions for measuring the electromagnetic response of electronic components on the strip using the instrument included in the kit.

In some embodiments, a kit can be used for environmental sampling. In some embodiments, a kit can be used for rapid detection of hazardous contaminants. In some embodiments, a kit can be used for detecting biothreats. In some embodiments, a kit can be used for testing the presence of contaminants in drinking water. In some embodiments, a kit can be used for detecting the presence of heavy metals in a medical test. In some embodiments, a kit can be used for detecting toxins in an environment.

While various embodiments of the methods and systems have been described, these embodiments are exemplary and in no way limit the scope of the described methods or systems. Those having skill in the relevant art may effect changes to form and details of the described methods and systems without departing from the broadest scope of the described methods and systems. Thus, the scope of the methods and systems described herein should not be limited by any of the exemplary embodiments and should be defined in accordance with the accompanying claims and their equivalents.

EXAMPLES

Example 1

Metamaterial Device Fabricated on a Paper-based Substrate

A paper based metamaterial (MM) device can be potentially utilized for quantitative analysis in biochemical sensing applications. Planar metallic resonators with minimum features of less than 5 μm have been fabricated on paper, using a photoresist-free shadow mask deposition technique. The fabricated paper metamaterial devices show unique electromagnetic (EM) resonant responses at predefined frequencies in dependence of the resonator size (i.e. Terahertz frequencies in the current case—1 THz=1012 Hz), which could be utilized as a signature for biochemical sensing applications. Proof of concept demonstrations were accomplished by monitoring the resonance shift induced by placing different concentrations of glucose solution on the paper metamaterials.

Example 2

Micrometer-sized Metamaterial Structures Deposited on Paper Via Stencils

As shown in FIGS. 1A-1C, the micrometer-sized metamaterial structures were deposited directly on the 280 μm thick paper substrates with predefined micro stencils. The micro stencils were fabricated using surface micromaching technology. The process consists of three main steps: a) deposition of SiNx thin film; b) patterning of the SiNx for the SRRs; and c) release of the SiNx thin film from backside by KOH etching. After fabrication of the stencils, the entire patterning/deposition process on paper is conducted in a dry, chemical-free environment preventing any possible contamination that might result from residues of the other photolithography based metal patterning steps (such as lift-off processes and wet etching). The stencils can be as large as a few $cm^2$ in the current case and could be even larger, depending on the quality of the pre-deposited silicon nitride film. While numerous samples were fabricated, we focus on three of samples with minimum feature size of less than 10 μm, including two purely electric resonators (#1, polarization sensitive electric resonator and #2, polarization non-sensitive electric resonator, both with a unit cell size of 100 μm×100 μm) and the canonical split ring resonators (#3, single SRR with a unit cell size of 50 μm×50 μm). A 1 mm wide silicon frame was kept on the edges as the supporting structure for later handling. The micro stencils were carefully attached to the paper substrates in contact mode.

A thin layer of 150 nm thick gold was then "sprayed" on the paper substrates uniformly at a rate of ~2 Å/s using electron-beam evaporation. The surface roughness of the paper substrate affects the pattern quality including both the minimum transferable linewidth and sharpness. In this work, photo paper (Epson glossy photo paper, Epson America, Inc.) with a surface roughness (Rq) less than 16 nm was used. For rougher paper, a thicker metal layer is needed to ensure the electrical conduction of the patterns.

The samples were cut into 1 cm×1 cm squares and a terahertz time-domain spectroscopy (THz-TDS) was used to characterize the electromagnetic responses. The measurements were performed at room temperature in a dry (<0.1% humidity) air atmosphere. The transmission of the THz electric field was measured for the sample and a reference. The electric field including both spectral amplitude and phase information were then calculated through Fourier transformation of the time-domain pulses. The TDS measurements were first carried out on a series of unpatterned paper substrates, and spectral transmission was obtained by dividing the sample by the reference, which in the present case is simply air. The paper substrates show high field transmission (larger than 45%) of terahertz radiation from 0.2 THz to 1.8 THz, as shown in FIG. 2. The samples were then mounted at normal incidence to the THz beam with the electric field perpendicular to the SRR gap and a bare paper substrate was use as the reference. As shown in FIG. 3, all three samples display strong resonances, which are comparable to those measured on semiconducting [23] and polymer substrates [24], at ~0.55 THz, 0.88 THz and 1.05 THz, respectively. These resonances are associated with the LC resonant response that arises from circulating currents driven by the electric field aligned perpendicular to the SRR gap. The resonant response is sensitive to the dielectric property modulation at the metal-dielectric interface where the EM field is largest.

FIG. 1 depicts: a) Schematic of the micrometer-sized metamaterial resonators "sprayed" on paper substrates with a pre-defined micro stencil; b) Photograph of a paper-based terahertz metamaterial sample; c) Optical microscopy image of one portion of as-fabricated paper metamaterial sample.

Figure 2:
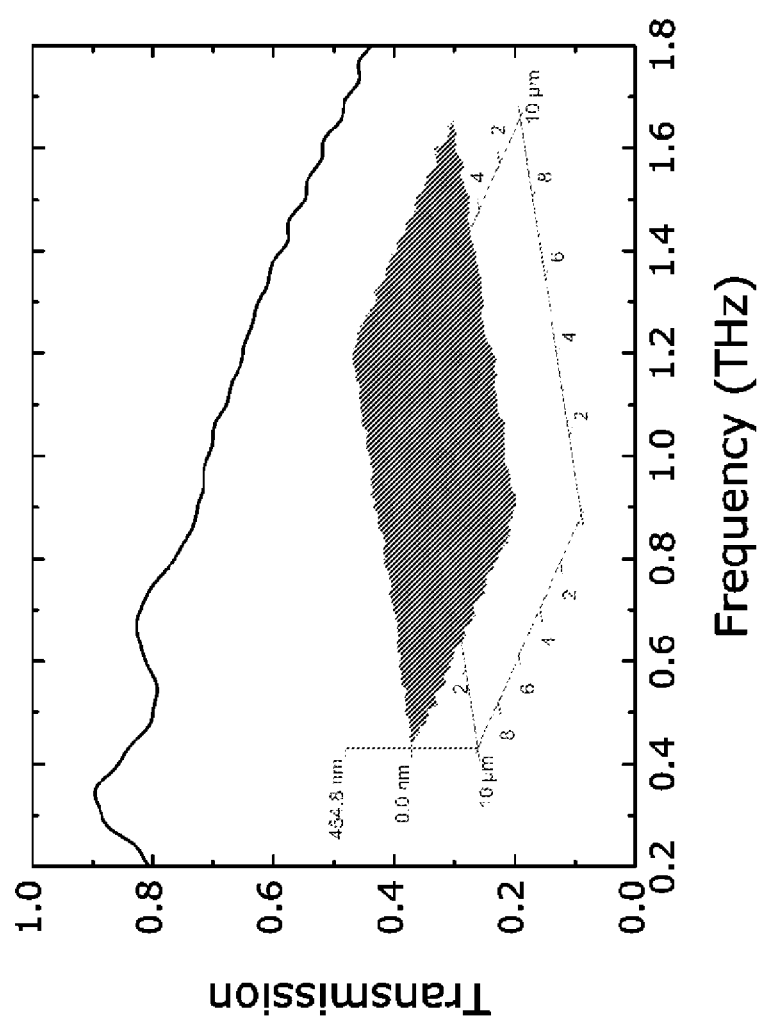
FIG. 2 depicts a graphical representation of the terahertz time domain spectroscopy (THz-TDS) characterized field transmission of electronic components fabricated on a 280-μm thick paper-based substrate, as well as a depiction of the atomic force microscopy (AFM) characterized surface roughness of the paper substrate.

FIG. 2 depicts terahertz time domain spectroscopy (THz-TDS) characterized field transmission of 280 μm thick pure paper substrates as a function of frequency from 0.2 THz to 1.8 THz. The inset includes atomic force microscopy (AFM) characterized surface roughness of the paper substrate.

Figure 3:
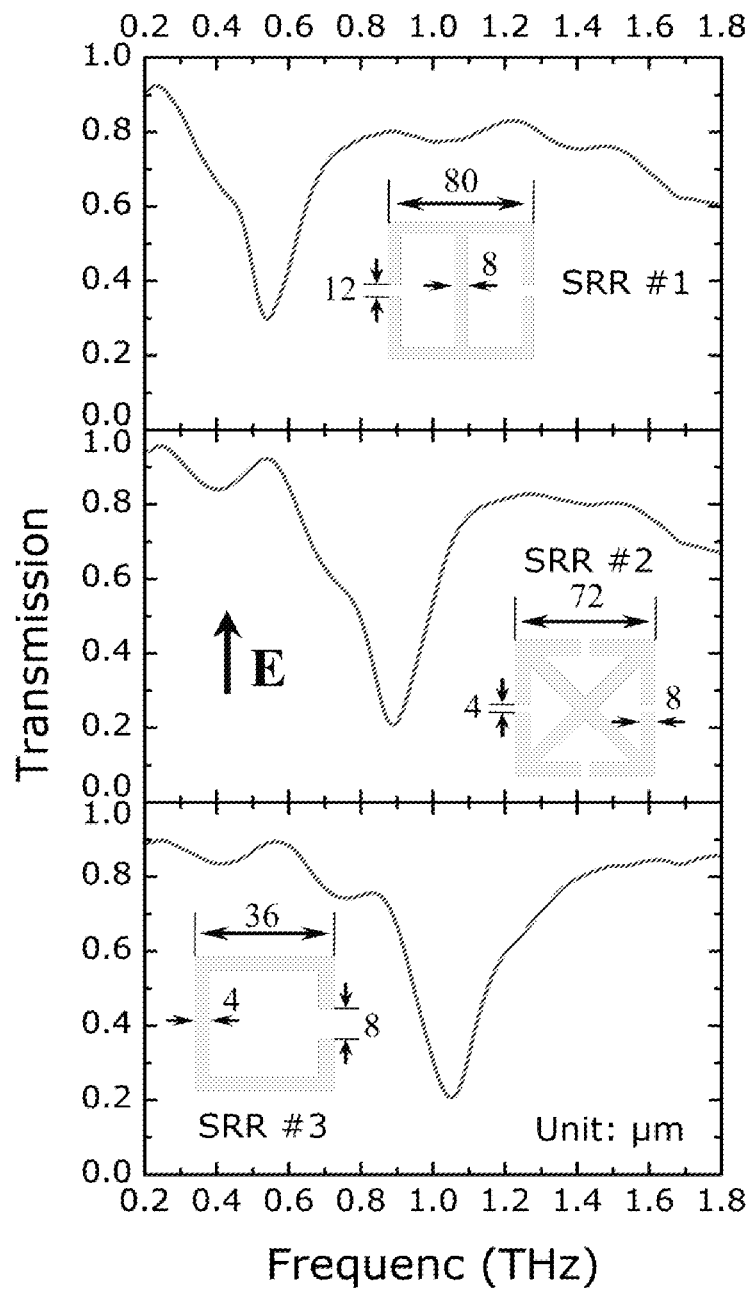
FIG. 3 depicts graphical representation of transmission spectra of electronic components fabricated on a paper-based substrate, as well as the designs and dimensions of the electronic components.

FIG. 3 depicts experimentally measured transmission spectra of the paper metamaterial samples as a function of frequency from 0.2 THz to 1.8 THz. The electric field (E) is aligned perpendicular to the SRR gap. The insets depicts designs and dimensions of the SRR elements.

Example 3

Metamaterials Fabricated on Paper for Sensing Glucose

Figure 4:
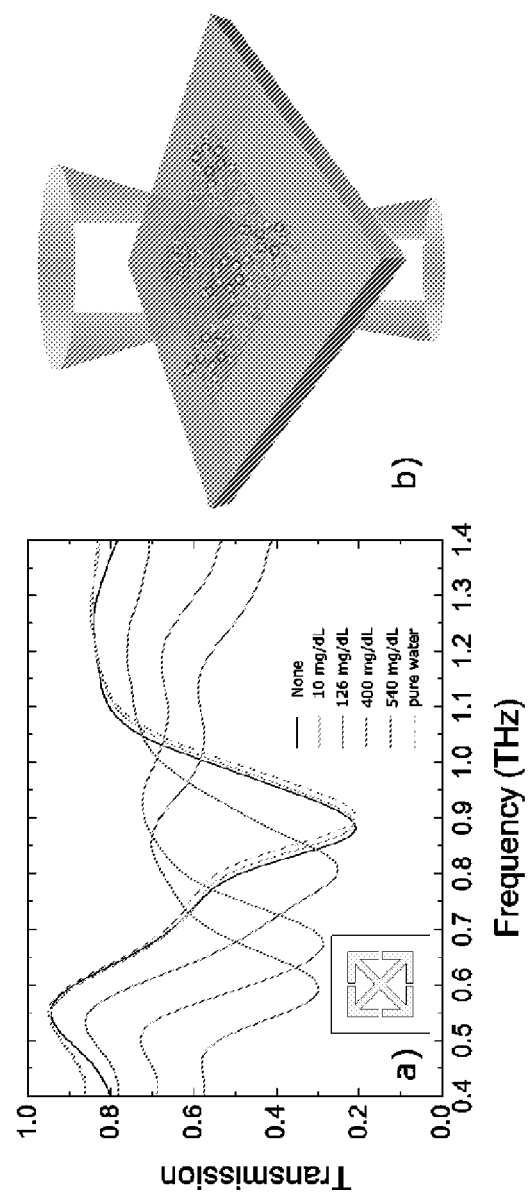
FIG. 4A depicts a graphical representation of the transmission spectra of metamaterials fabricated on a paper-based substrate when the metamaterials have been coated with a series of glucose solutions with varying concentration.
FIG. 4B depicts a schematic of the testing site used to obtain the transmission spectra of FIG. 4A.

Proof of concept demonstrations of the use of paper metamaterials as sensors were performed by coating the paper metamaterials with a glucose solution with concentration varying from 126 mg/dL (7 mmol/L, within normal range in postprandial human blood) to 540 mg/dL (30 mmol/L, considered as severe hyperglycemia which can pose serious health threats to diabetics and may threaten metal functions.). The glucose solutions were prepared by mixing the glucose crystals into de-ionized water. Metamaterial samples with SRR design #2 (with reference to FIG. 3) were used for the sensing experiments. Glucose solution with a volume of ~100 μL was deposited on the resonators and allowed to dry in air. Full drying was determined by a high precision scale showing no further variation in weight. The transmission spectra were then measured by THz-TDS as a function of frequency. With higher glucose concentration, the analyte-induced resonance should shift more since the shift is mainly due to alterations in the SRR capacitance and can be calculated by the equation of. This was verified by the experimental results, as shown in FIG. 4. A resonance at 881GHz was observed for the paper metamaterial sample without coating and this value shifted continuously to lower frequencies as the concentration of the glucose solution increased. A maximum shift of ~300 GHz was observed on the 540 mg/dL glucose solution coated sample.

The performance of the paper metamaterial at low glucose levels was investigated by adding a diluted glucose solution of 10 mg/dL and measuring the resonance shift. A blue shift from 881 GHz to 891 GHz was observed, which was in the opposite direction from other experiments with relatively high glucose levels shifting to lower frequencies. This may be caused by the change of the paper substrate induced by the water content in the glucose solution. A 100 μL solution of pure water was therefore cast on one paper metamaterial sample and the transmission spectra were measured and compared before and after the coating. Experiments were repeated and a blue shift of ~20 GHz to the higher frequency was constantly observed, while no shift was found on same resonators fabricated on silicon substrates. This could be attributed to the perfusion of a small amount of water into the paper substrates during the drying which changes the dielectric properties and/or the shape of the paper slightly, consequently reducing the capacitance of the SRRs. Nonetheless, this indicates that the observed shifts on previous samples (from 126 mg/dL up to 540 mg/dL), which were more significant and towards lower frequencies, were induced mainly by the glucose and could be therefore useful as the basis to develop a paper metamaterial sensor.

For small changes in dC, the resonance shift do) can be approximated as a linear response that decreases as the amount of analyte increases (which increases the base capacitance diluting the change). In this case, keeping into account the base shift due to the water, the paper metamaterial has a sensitivity of $$\sim 0.95 \frac{\text{GHz}}{\frac{\text{mg}}{\text{dL}}},$$

defined as the resonance shift (Δf) per glucose concentration variation (Δg) This value is obtained by using the equation of $$\frac{\Delta f}{\Delta g}$$

for glucose levels up to 126 mg/dL, and the sensitivity dropped to $$\sim 0.59 \frac{\text{GHz}}{\frac{\text{mg}}{\text{dL}}}$$

for glucose levels up to 540 mg/dL. While glucose levels of 10 mg/dL were repeatedly measured in these experiments, the minimum possible measurable frequency change for our current experimental configuration is ~5 GHz, which corresponds to ~5 mg/dL (i.e. 5% with a base glucose level of 100 mg/dL). The sensitivity of the metamaterials could be further improved and optimized by a variety of strategies with different SRR geometries and could be particularly relevant for applications of this technique in physiological glucose measurements given the necessity, among other things, for accuracy at lower glucose concentrations [25].

Further, the sensing modality of paper-based metamaterials reported in this work is based on changes in the capacitance of the SRRs which is mainly determined by the dielectric properties and the thickness/volume of the analyte embedded in the paper structure. Whereas the sensitivity is appreciable in this single-analyte case, inference with other substances will cause a different response of the device. This effect can be mitigated by acquiring individual references for all other possible interferent substances as a "relevant" measurement. A more general (and probably more realistic) way is to include a reagent (for example glucose oxidase, which is widely used on commercial devices for blood glucose sensing), which favors a chemical reaction more specific to the target analyte. The ensuing chemical reaction will alter the dielectric properties of the material and be transduced by the paper-based metamaterial structure described here. Furthermore, since it is found that coupled resonances can significantly change the overall response to small perturbations to the system, it is possible to design the SRRs to match the resonant frequency of the desired sensing target to further improve sensitivity and selectivity [26].

Some results of glucose sensing using paper-based MMs showed sensitivity of $$\sim 0.95 \frac{\text{GHz}}{\frac{\text{mg}}{\text{dL}}},$$

and an associated ability to experimentally measure glucose level of 10 mg/dL, which can be further improved by optimizing the SRRs geometries and the characterization system.

FIG. 4 depicts a) Experimentally measured transmission spectra of the paper metamaterial samples coated with a series of glucose solution with varying concentrationas a function of frequency from 0.4 THz to 1.4 THz; b) Schematic of the testing setup. The inset depicts a schematic of as-used SRR element.

Example 4

Micro Stencil Fabrication of Electronic Components on a Paper-based Substrate

Figure 5:
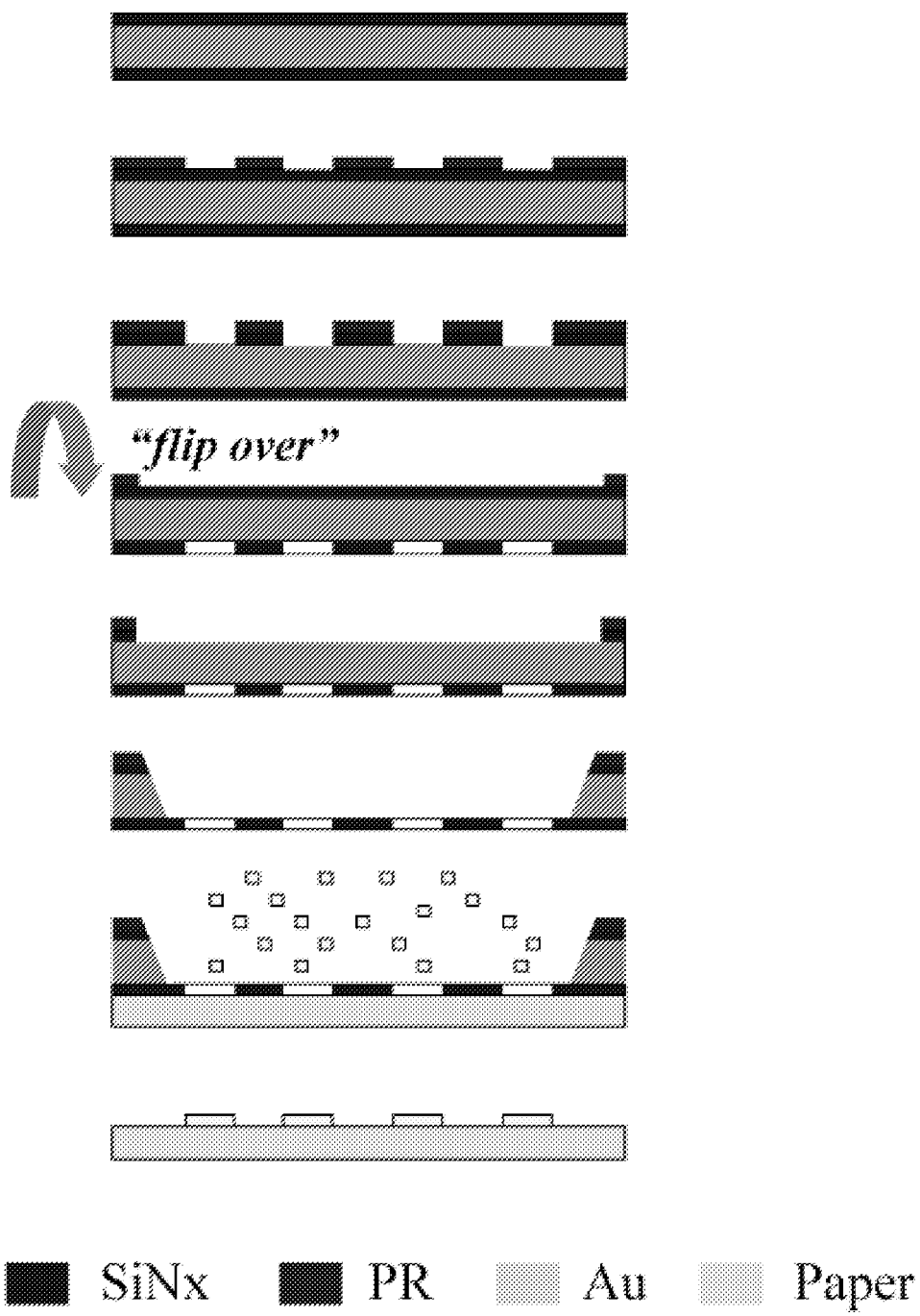
FIG. 5 depicts diagrams of the fabrication of metamaterials on a paper-based substrate.

The fabrication of paper based metamaterials is shown in FIG. 5. The micro stencils with the desired metamaterial patterns were fabricated on a commercially purchased 4" silicon wafers with 400 nm thick LPCVD pre-deposited super low stress silicon nitride (SiNx) films on both sides. The SRRs were patterned using standard UV photolithography with Shipley S1813 PR on the top side of the wafer, followed by reactive ion etching (RIE) using Sulfur hexafluoride (SF6) and Helium (He) at 110 w for 6 minutes with the PR as the etching mask to define the stencil patterns. The wafer was then flipped over and open windows for backside wet etchingwere patterned with a similar process as mentioned above. This was followed by rinsing in a stirred 25% concentrated KOH solution at 70° C. for a few hours. The suspended stencil structures were released when KOH etched through the wafer from the backside and reached the SiNx film on the top side. The stencils can be as large as a few cm2 in our case and could be even larger, depending on the quality of the pre-deposited silicon nitride film. In this work, we patterned 7×7 stencil array on the 4" silicon wafer. Each stencil is approximately 1 cm×1 cmin area with the SRR array approximately 8 mm×8 mm in the center. A 1 mm wide silicon frame was kept on the edges as the supporting structure for later handling. The micro stencils were carefully attached to the 80 μm thick silk films in contact mode. A thin layer of 150 nm thick gold was then "sprayed" on the silk substrates uniformly at a rate of ~2 Å/s using electron-beam evaporation.

Example 5

Electronic Components Fabricated on Newsprint

Figure 6:
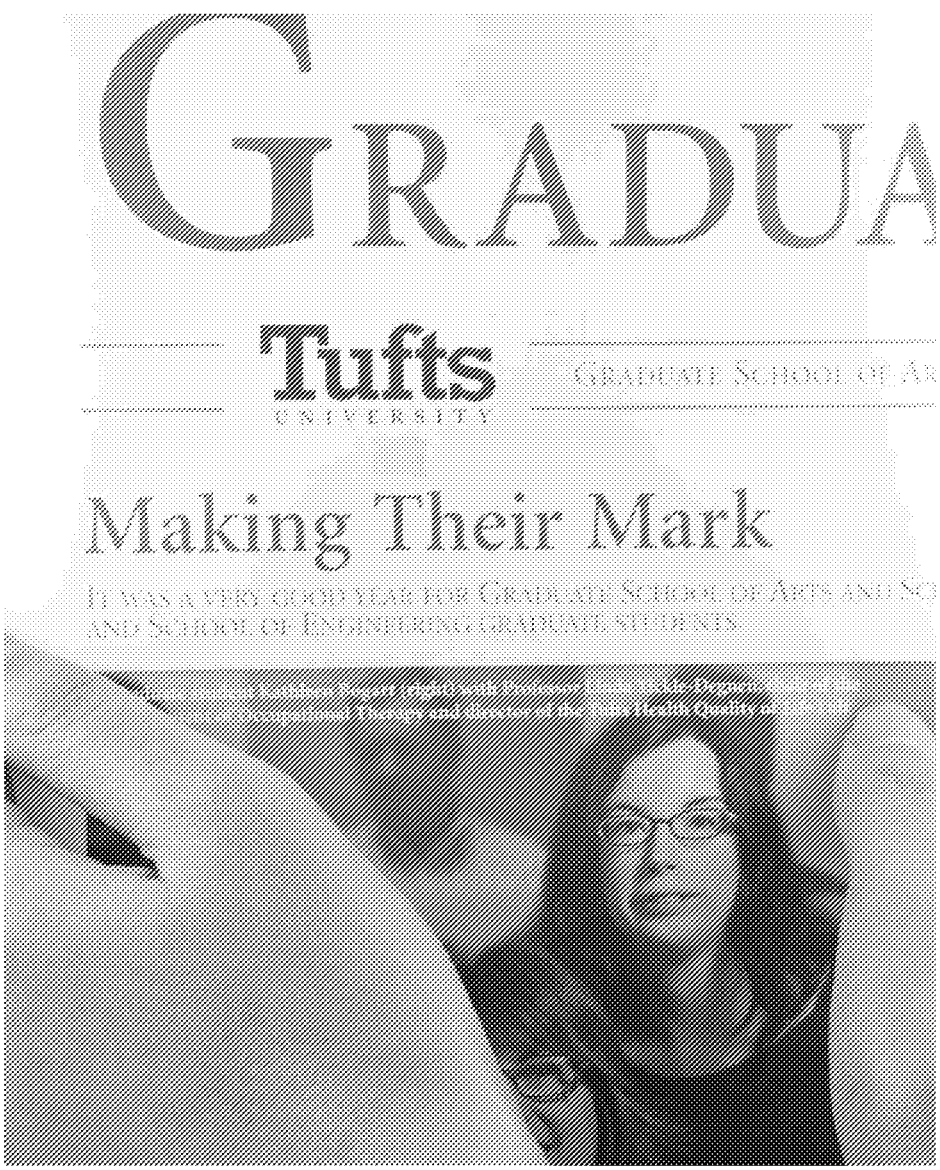
FIG. 6 depicts an array of micro-split ring resonators fabricated on a newspaper.

FIG. 6 depicts an array of micro-split ring resonators fabricated on a newspaper.

Example 6

Figure 7:
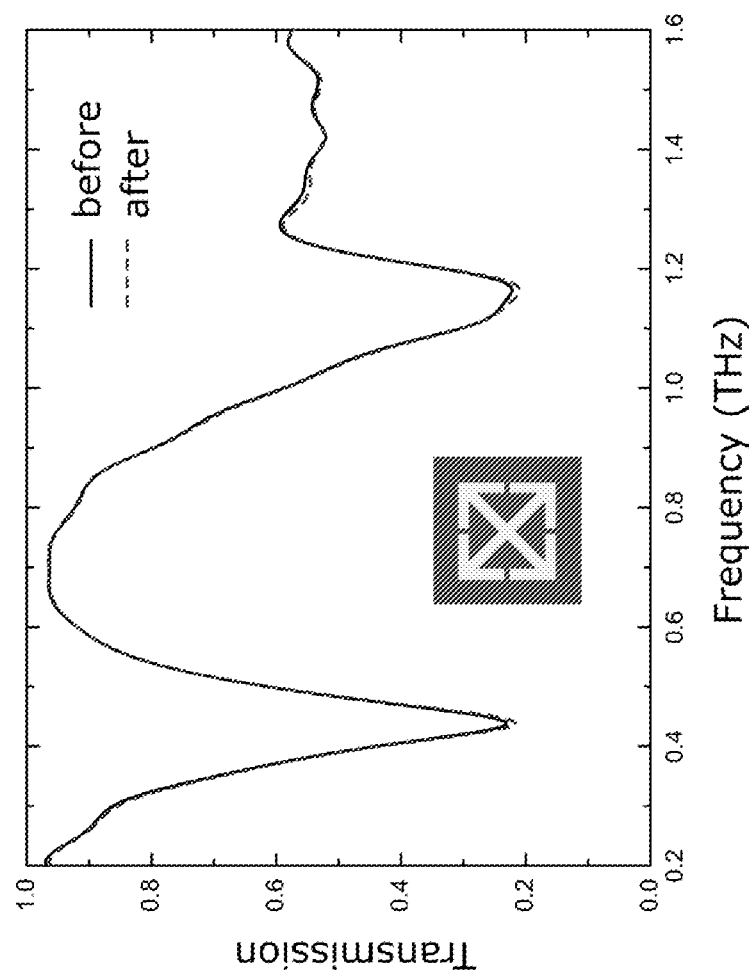
FIG. 7 depicts a graphical representation of the transmission spectra of electronic components based on silicon substrates before and after adding 100 μL of deionized water.

Effect of Rinsing on Electronic Components Fabricated on Silicon Substrate, for Comparison FIG. 7 depicts a graphical representation of the transmission spectra of electronic components based on silicon substrates before and after adding 100 μL of deionized water.

REFERENCES

[1] C. D. Chin, V. Linder, S. K. Sia, Lab Chip 2007, 7, 41.
[2] P. Yager, T. Edwards, E. Fu, K. Helton, K. Nelson, M. R. Tam, B. H. Weigl, Nature 2006, 442, 412.
[3] J. G. E. Gardeniers, A. Van den Berg, Anal. Bioanal. Chem. 2004, 378, 1700.
[4] A. Escarpa, M. C. Gonzalez, A. G. Crevillen, A. J. Blasco, Electrophoresis 2007, 28, 6.
[5] D. V. Lim, J. M. Simpson, E. A. Kearns, M. F. Kramer, Clin. Microbiol. 2005, 18, 583.
[6] E. Oosterbroek, A. Van Den Berg, in Lab-on-a-Chip: Miniaturized Systems for (Bio)chemical Analysis and Synthesis, Elsevier Science, 2003.
[7] H. Moon, A. R. Wheeler, R. L. Garrell, J. A. Loo, C. J. Kim, Lab Chip 2006, 6, 9.
[8] G. M. Whitesides, Nature 2006, 442, 7101.
[9] A. W. Chow, AIChE J. 2002, 48, 8.
[10] D. Figeys, D. Pinto, Anal. Chem. 2000, 72, 9.
[11] W. Dungchai, O. Chailapakul, C. S. Henry, Anal. Chem. 2009, 81, 14.
[12] W. Zhao, A. Van den Berg, Lab Chip 2008, 8, 12.
[13] D. Mabey, R. W. Peeling, A. Ustianowski, M. D. Perkins, Nat. Rev. 2004, 2, 231.
[14] F. Yue, T. S. Ngin, G. Hailin, Sensor Actuat. B-Chem. 1996, 32, 1.
[15] I. Macgillivray, J. E. Tovey, BJOG-Int. J. Obstet.-Gy. 1957, 64, 3.
[16] A. W. Martinez, S. T. Phillips, M. J. Butte, G. M. Whitesides, Angew. Chem. Int. Ed. 2007, 46, 1318.
[17] D. A. Bruzewicz, M. Reches, G. M. Whitesides, Anal. Chem. 2008, 80, 3387.
[18] A. W. Martinez, S. T. Phillips, E. Carrilho, S. W. Thomas III, H. Sindi, G. M. Whitesides, Anal. Chem. 2008, 80, 3699.
[19] D. R. Smith, W. J. Padilla, D. C. Vier, S. C. Nemat-Nasser, S. Schultz, Phys. Rev. Lett. 2000, 84, 4184.
[20] W. J. Padilla, D. N. Basov, D. R. Smith, Mater. Today 2006, 9, 28.
[21] J. F. O'Hara, R. Singh, I. Brener, E. Smirnova, J. Han, A. J. Taylor, W. Zhang, Opt. Express 2008, 16, 3.
[22] K. Abe, K. Suzuki, D. Citterio, Anal. Chem. 2008, 80, 18.
[23] W. J. Padilla, M. T. Aronsson, C. Highstrete, M. Lee, A. J. Taylor, R. D. Averitt, Phys. Rev. B 2007, 75, 041102R.
[24] H. Tao, A. C. Strikwerda, K. Fan, C. M. Bingham, W. J. Padilla, X. Zhang, R. D. Averitt, J. Phys. D: Appl. Phys. 2008, 41, 232004.
[25] J. Hones, P. Muller, N. Surridge, Diabetes Technol The. 2008, 10, Supplement 1.
[26] C. M. Bingham, H. Tao, X. Liu, R. D. Averitt, X. Zhang, W. J. Padilla, Opt. Express 2008, 16, 23.
[27] J. Barber, D. E. Hooks, D. J. Funk, R. D. Averitt, A. J. Taylor, D. Babikov, J. Phys. Chem. A. 2005, 109, 3501.
[28] S. Preradovic, I. Balbin, N. C. Karmakar, G. F. Swiegers, IEEE T. Microw. Theory 2009, 57, 5.
[29] P. Calvert, Chem. Mater. 2001, 13, 3299.

What is claimed is:

1. An apparatus comprising:
   a paper-based substrate; and
   at least one geometrically patterned conductive structure deposited on and directly coupled to the paper-based substrate, the at least one geometrically patterned conductive structure configured to provide a resonant response that is at least partially dependent on a size of the at least one geometrically patterned conductive structure, wherein a particular geometrically patterned conductive structure of the at least one geometrically patterned conductive structure extends for at least 10 µm in a first direction and at least 10 µm in a second direction perpendicular to the first direction,
   wherein the at least one geometrically patterned conductive structure responds to incident electromagnetic radiation to provide the resonant response,
   wherein when the apparatus is exposed to one or more environments or one or more environmental factors, the exposure induces a change in the resonant response.

2. The apparatus of claim 1, wherein the paper-based substrate has a surface roughness greater than 10 nm.

3. The apparatus of claim 1, wherein the paper-based substrate comprises wood pulp.

4. The apparatus of claim 1, wherein the paper-based substrate comprises a biocompatible component.

5. The apparatus of claim 1, wherein the paper-based substrate comprises a dopant.

6. The apparatus of claim 5, wherein the dopant is a biological element.

7. The apparatus of claim 5, wherein the dopant is a pharmaceutical, antibody, fragment or portion of an antibody, antibiotic, enzyme, organic indicator, photoactive dye, cell, protein, peptide, nucleic acid analogue, nucleotide, oligonucleotide, peptide nucleic acid, aptamer, hormone, hormone antagonist, growth factor, fragment of a growth factor, variant of a growth factor, recombinant growth factor, fragment of a recombinant growth factor, variant of a recombinant growth factor, cytokine, antimicrobial compound, virus, antiviral, toxin, prodrug, drug, chemotherapeutic agent, small molecule, chromophore, light-emitting organic compound, light-emitting inorganic compounds, light-harvesting compound, light-capturing complex, or combinations thereof.

8. The apparatus of claim 5, wherein the dopant modulates the incident electromagnetic radiation.

9. The apparatus of claim 1, wherein the at least one geometrically patterned conductive structure directly coupled to the paper-based substrate is disposed on a surface of the paper-based substrate.

10. The apparatus of claim 1, wherein the at least one geometrically patterned conductive structure directly coupled to the paper-based substrate is embedded in the paper-based substrate.

11. The apparatus of claim 1, wherein the at least one geometrically patterned conductive structure comprises a conductive material.

12. The apparatus of claim 11, wherein the conductive material comprises gold, aluminum, chromium, silver, platinum, copper, titanium, nickel, rhodium, cobalt, magnesium, iron, zirconium, molybdenum, palladium, hafnium, iridium, tungsten, tantalum, indium tin oxide (ITO), polysilicon, graphite, or any combination thereof.

13. The apparatus of claim 1, wherein the at least one geometrically patterned conductive structure forms or comprises a resonator, split-ring resonator, polarization-sensitive electric resonator, polarization non-sensitive electric resonator, radio-frequency identification (RFID) device, metamaterial structure, antenna, conductive coil, an electrode, a passive electronic, a thin film semiconductor component, a solar cell, a capacitor, an inductor, a resistor, an LED, a transistor, a conductive coil, a coil that receives power, a photodetector, a VCSEL, a thin film electronic, a resonator cavity, or any combination thereof.

14. The apparatus of claim 1, wherein the apparatus responds to microwave radiation, infrared radiation, visible radiation, ultraviolet radiation, or any combination thereof.

15. The apparatus of claim 1, wherein the apparatus responds to the incident electromagnetic radiation to exhibit an electromagnetic signature in the terahertz (THz) frequencies, megahertz (MHz) frequencies, gigahertz (GHz) frequencies, petahertz (PHz) frequencies, or any combination thereof.

16. The apparatus of claim 1, wherein the apparatus responds to the incident electromagnetic radiation to exhibit an electromagnetic signature, the electromagnetic signature comprising the resonant response.

17. The apparatus of claim 1, wherein the apparatus modulates the incident electromagnetic radiation.

18. The apparatus of claim 1, which is a onetime-use disposable product.

19. A kit comprising the apparatus of claim 1.

20. The apparatus of claim 1, wherein the at least one geometrically patterned conductive structure is an array of metamaterial elements.

21. The apparatus of claim 20, wherein elements of the array of metamaterial elements are sized such that at least one dimension is sub-wavelength.

22. The apparatus of claim 1, wherein oscillations of oscillating electrons in the at least one geometrically patterned conductive structure exhibit a specific resonant response according to the at least one geometrically patterned conductive structure's electrical permittivity and/or magnetic permeability.

23. The apparatus of claim 1, wherein the one or more environments or one or more environmental factors that induce the change are chemical, biochemical, temperature, mechanical strain, gas concentration, gas release, surface reactions, bulk reactions, hydration, material removal, or any combination thereof.

24. The apparatus of claim 1, wherein the one or more environments or one or more environmental factors that induce the change are targets or target substances for detection.

25. The apparatus of claim 24, wherein the targets or target substances are bacteria, hazardous contaminants, toxins, heavy metals, or glucose.

26. The apparatus of claim 24, wherein the targets or target substances are bioterrorism agents.

27. The apparatus of claim 1, wherein the change in the resonant response of the at least one geometrically patterned conductive structure varies with a geometry of the at least one geometrically patterned conductive structure, its geometric scale, dielectric properties of the at least one geometrically patterned conductive structure and/or the paper-based substrate, dopants coupled to or embedded within the paper-based substrate, or any combination thereof.

28. The apparatus of claim 1, wherein the resonant response comprises a fingerprint that identifies a chemical or biochemical agent.

29. The apparatus of claim 1, wherein a feature comprises a first conductive portion of the portion of the particular geometrically patterned conductive structure and a second conductive portion of the particular geometrically patterned conductive structure, the first conductive portion being arranged in parallel with the second conductive portion, and the dimension being a distance between the first conductive portion and the second conductive portion.

30. The apparatus of claim 1, wherein a feature of the particular geometrically patterned conductive structure extends between 200 nm-500 nm along a dimension of the feature.

* * * * *